United States Patent
Prestel

(10) Patent No.: US 6,814,745 B2
(45) Date of Patent: Nov. 9, 2004

(54) SURGICAL INSTRUMENT WITH ADJUSTABLE TOOL FOR GRIPPING, HOLDING OR CUTTING BODY TISSUE OR THE LIKE

(75) Inventor: Stephan Prestel, Rheinstetten-Mörsch (DE)

(73) Assignee: Richard Wolf GmbH, Knittlingen (DE)

( * ) Notice: Subject to any disclaimer, the term of this patent is extended or adjusted under 35 U.S.C. 154(b) by 166 days.

(21) Appl. No.: 10/039,506

(22) Filed: Jan. 4, 2002

(65) Prior Publication Data

US 2002/0095176 A1 Jul. 18, 2002

(30) Foreign Application Priority Data

Jan. 18, 2001 (DE) .......................... 101 02 089

(51) Int. Cl.⁷ .................................... A61B 17/28
(52) U.S. Cl. ......................................... 606/205
(58) Field of Search ......................... 606/142, 208, 606/171

(56) References Cited

U.S. PATENT DOCUMENTS

| 4,412,539 A | * | 11/1983 | Jarvik .................... 606/143 |
| 4,467,802 A | | 8/1984 | Maslanka |
| 4,674,501 A | * | 6/1987 | Greenberg ............... 606/174 |
| 5,084,054 A | * | 1/1992 | Bencini et al. .......... 606/113 |
| 5,376,094 A | | 12/1994 | Kline |
| 5,489,288 A | * | 2/1996 | Buelna ................... 606/144 |
| 6,162,207 A | | 12/2000 | Ouchi |
| 6,176,853 B1 | * | 1/2001 | Stolyarenko ............ 606/1 |
| 6,221,083 B1 | * | 4/2001 | Mayer ................... 606/139 |

FOREIGN PATENT DOCUMENTS

| DE | 30 12 447 A1 | 10/1981 |
| DE | G 84 15 222.2 | 9/1984 |
| DE | 36 32 786 A1 | 3/1988 |
| EP | 0 446 020 A1 | 9/1991 |

* cited by examiner

Primary Examiner—David O. Reip
Assistant Examiner—Bradford C Pantuck
(74) Attorney, Agent, or Firm—Akin Gump Strauss Hauer & Feld, L.L.P.

(57) ABSTRACT

A surgical instrument has a tool located at the distal instrument end, a stationary first grip part at the proximal instrument end, a second grip part adjustable in an axially guided manner in the form of a reel, and an actuation element for the tool. The actuation element in connection with the second grip part is axially adjustable on adjustment of the second grip part. For improving the handling of the instrument, it is envisaged that, by way of a lever system linked onto the second grip part and a stationary part of the instrument, the adjustment path of the second grip part is geared down and the force exerted onto the second grip part is transmittable, geared up, to the actuation element.

4 Claims, 2 Drawing Sheets

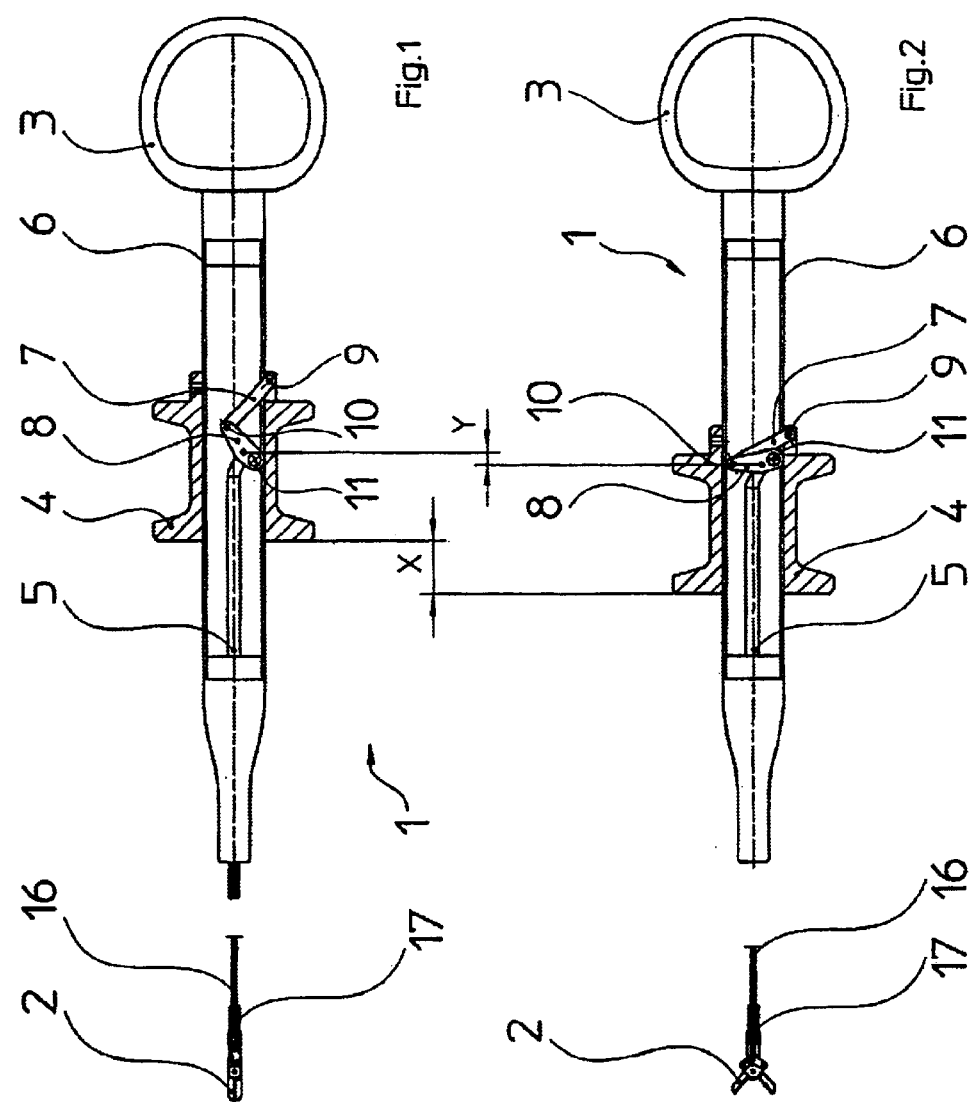

SURGICAL INSTRUMENT WITH ADJUSTABLE TOOL FOR GRIPPING, HOLDING OR CUTTING BODY TISSUE OR THE LIKE

BACKGROUND OF THE INVENTION

The invention relates to a surgical instrument with a tool which is located at the distal instrument end, with a stationary first grip part at the proximal instrument end, with an axially guided second grip part in the form of a reel, and with an actuation element for the tool, wherein the actuation element in connection with the second grip part is axially adjustable on adjustment of the second grip part.

A surgical instrument of the generic type is known from German Utility Model DE 84 15 222 U1. Here, a forceps at the distal end of the instrument is actuated by the surgeon carrying out a displacement movement between an axially fixed grip part and a reel. This displacement movement is transmitted via a wire led in a sleeve to the forceps, which then is correspondingly closed or opened.

A similar design has the surgical gripping element known from German published patent application DE 30 12 447 A1. Here also, a wire led in a sleeve transmits an axial displacement movement of a reel relative to the stationary grip to the tool. The wire is connected to the stationary grip and the reel to the actuation-side end of the sleeve, wherein the latter mentioned connection is created via a direction-reversal gearing.

With the known instruments, in particular with the application of smaller forceps, it is disadvantageous that, on account of the comparatively small displacement path of the reel relative to the stationary grip, a fine-touch actuation of the forceps jaw or a scissors arranged in place of the forceps is not possible. This is caused on account of the relatively short jaw part limbs and connecting rod, on which the pull wire engages with its distal end and whose proximal end is connected to the reel.

BRIEF SUMMARY OF THE INVENTION

It is therefore the object of the present invention to develop further a surgical instrument of the generic type, such that the handling of the instrument is improved and a more fine-touch actuation of the instrument is possible. In particular with the application of smaller forceps, it should be possible to ensure a fine-touch actuation of the forceps jaw, which is still accurate.

The solution of this object by way of the invention is characterized in that by way of a lever system linked onto the second grip part and a stationary part of the instrument the adjustment path is geared down and the force exerted onto the reel is transmittable, geared up, to the actuation element.

The lever system may comprise two levers. With this in an advantageous manner, the one first lever with its one end is articulately arranged on the second grip part and with its other end is articulately arranged on the other second lever; the second lever with its one end is articulately arranged on the first lever and with its other end is articulately arranged on the stationary part of the instrument; and finally, the actuation element is articulately fastened between the two linkage points of the second lever.

Alternatively, the lever system may also comprise a single lever. With this the lever with its one end is articulately arranged on the stationary part of the instrument and with its other end is slidingly arranged in a guide of the second grip part; and the actuation element is articulately fastened between the two ends of the lever to this lever. The guide at the same time comprises a bore, which extends essentially perpendicular to the movement direction of the actuation element. It can in particular comprise a cylindrically formed section and a conically formed section connecting to this lever.

As an overload protection between the lever system and the actuation element, there may be arranged a spring element.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is longitudinal view, partially in section and partially broken away, of a surgical instrument of the invention with a closed tool;

FIG. 2 is a longitudinal view of the surgical instrument, corresponding to the representation according to FIG. 1, with an opened tool;

DETAILED DESCRIPTION OF THE INVENTION

Figure 5:
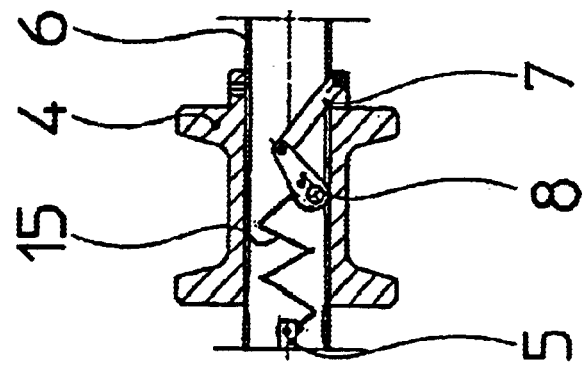
FIG. 5 is a sectional cutout view similar to FIG. 3 of a further embodiment with a spring element.

In FIG. 1 there is to be seen the surgical instrument 1 which at its distal end comprises a tool 2. The tool 2 is here formed as a forceps. It has a forceps jaw with two jaw parts which are pivotable towards one another by actuation of the instrument 1, for opening and closing the forceps jaw, as will later be described in more detail. Alternatively—but not shown—the tool may also be designed as a scissors in order to cut tissue.

The instrument 1 comprises a first, stationarily arranged grip part 3 in the form of a ring which is gripped through by the thumb of the surgeon. A second grip part 4 is axially adjustable relative to the first grip part 3 and is formed as a reel, which is gripped between the index finger and the middle finger and which permits a particularly simple handling.

With an axial displacement of the reel 4 relative to stationary grip part 3, there is effected an axial displacement of an actuation element 5, which is formed as a rod and which, in its continuation in the direction of the distal end of the instrument 1, merges into a wire 16. The wire 16 is guided in a sleeve 17 according to the principle of a Bowden cable, wherein the sleeve 17 may be designed as a wire coil and the distal wire end in the known manner is connected to the tool.

The actuation element 5 at its proximal end facing the first grip part 3 is articulately in connection with a lever system. This lever system consists, in the case of the embodiment according to the FIGS. 1, 2, 3 and 5, of two levers 7 and 8.

The one first lever 7 is with its one end linked to a first linkage point 9 on the reel 4; while its other end is connected at a linkage point 10 to the other second lever 8. The latter is in turn at the linkage point 11 connected to a stationary part of the instrument 1, in the present case on the inner circumference of the tube 6 on which the reel is guided.

The manner of functioning resulting from this design is also clear with a comparison of FIGS. 1 and 2. The two Figures are aligned with one another such that the instrument with its parts 3, 6 and 11 located in the same axial position. According to FIG. 1 the reel 4 in comparison to FIG. 2 is pulled to the right or proximally so that the tool 2 is closed. For opening the tool 2 the reel 4 is displaced distally on the tube 6, and specifically into the position according to FIG. 2 in which the tool 2 is opened. With these procedures the position of the linkage point 11 is maintained while all other joints or linkage points and also the two levers 7 and 8 assume changing positions according to the representations, wherein according to the movement direction of the reel 4 the actuation element 5 is adjusted axially distally or proximally for opening and closing the tool 2.

As furthermore appears from a comparison of the two Figures, the reel with the movement from its extreme position to the left—tool 2 opened—displaced into its extreme right position—tool 2 closed—is displaced by the path X. As a result of the selected geometry of the lever system 7 and 8, as well as the linked arrangement of the actuation element 5 between the two linkage points 10 and 11, in the specific embodiment example, it results that the actuation element 5 is displaced merely by the path Y. This means that, on the one hand, the displacement path of the actuation element 5 in relation to that of the reel 4 is geared down and, on the other hand, the forces which are exerted onto the reel 4 are geared up in relation to the actuation force of the actuation element 5.

Accordingly, with the instrument put forward it is possible to achieve a fine-touch actuation of the tool 2, and in spite of this, it is possible to exert relatively large forces onto the actuation element on closing the tool.

Figure 4:
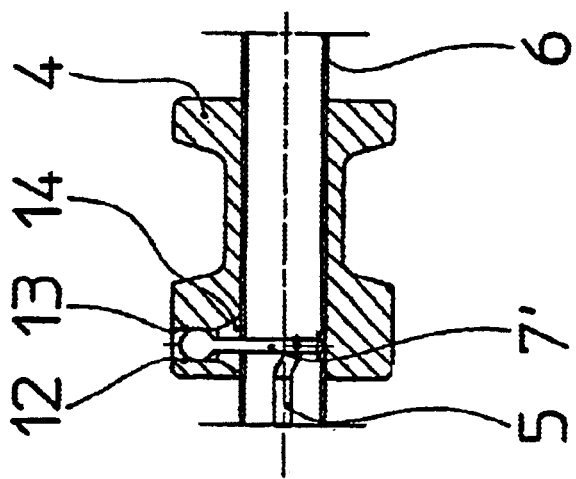
FIG. 4 is sectional cutout view of an embodiment of the lever system alternative to FIG. 3.
Figure 3:
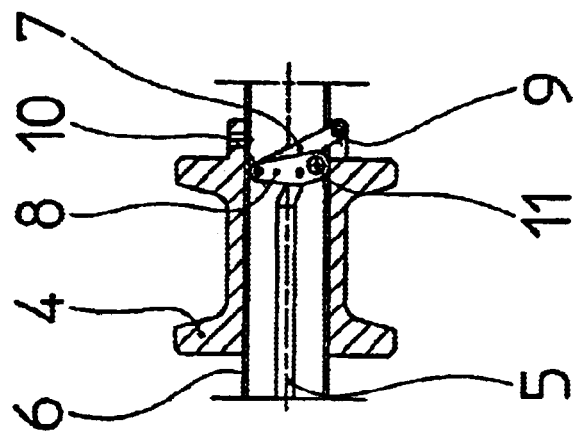
FIG. 3 is a sectional cutout view of the instrument with a reel as a second grip part and lever system.

FIG. 4 shows a lever system which only consists of a single lever 7'. The lever 7' is with its one end articulately fastened to the stationary part 6 of the instrument. Its other end is formed as a ball-shaped head and is arranged in a guide 12, which is incorporated into the reel 4. The guide 12 at the same time in its upper part consists of a cylindrical section 13, which in the lower part blends into a spherical section 14. On displacement of the reel 4 relative to the stationary part 6, the ball-shaped end of the lever 7' slides in the guide 12. At the same time there results a pivoting movement of the lever 7' gripping through a slot in the tube 6. The actuation element 5 linked on between the two ends of the lever 7' is at the same time displaced correspondingly geared down.

FIG. 5 shows finally yet a further embodiment, which may be applied with all mentioned lever systems. The actuation element 5 here is not directly arranged on the lever 8 or 7'. The connection between the lever 8 or 7' to the actuation element 5 is rather created by a spring element 15.

The spring element 15 serves as an overload protection of the instrument. With this the element 15 on closing the tool which, e.g., grasps tissue is loaded in tension.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A surgical instrument comprising a tool which is located at a distal instrument end, a stationary first grip part at a proximal instrument end, a second grip part adjustable in an axially guided manner in a form of a reel, an actuation element for the tool, wherein the actuation element is axially adjustable on adjustment of the second grip part, and a lever system linked to the second grip part and a stationary part of the instrument, wherein the lever system comprises first and second levers, the first lever having one end articulately linked on the second grip part and another end articulately linked on the second lever, the second lever having one end articulately linked on the first lever and another end articulately linked on the stationary part of the instrument, and the actuation element being articulately fastened between the two linkage points of the second lever, such that the lever system acts as a path reducing gear with respect to an adjustment path of the second grip part and acts as a force increasing gear with respect to a force transmitted from the second grip part to the actuation element.

2. The surgical instrument according to claim 1, wherein a spring element is arranged between the lever system and the actuation element.

3. A surgical instrument comprising a tool which is located at a distal instrument end, a stationary first grip part at a proximal instrument end, a second grip part adjustable in an axially guided manner in a form of a reel, an actuation element for the tool, wherein the actuation element is axially adjustable on adjustment of the second grip part, and a lever system linked to the second grip part and a stationary part of the instrument, wherein the lever system comprises one lever having one end articulately linked on the stationary part of the instrument and another end slidingly arranged in a guide of the second grip part, wherein the guide comprises a bore which extends essentially perpendicular to a movement direction of the actuation element and further comprises a cylindrical section and a conical section connected thereto, and the actuation element being articulately linked to the lever between the two ends of the lever, such that the lever system acts as a path reducing gear with respect to an adjustment path of the second grip part and acts as a force increasing gear with respect to a force transmitted from the second grip part to the actuation element.

4. The surgical instrument according to claim 3, wherein a spring element is arranged between the lever system and the actuation element.

* * * * *